US012767629B2

(12) United States Patent
Kase et al.

(10) Patent No.: US 12,767,629 B2
(45) Date of Patent: Oct. 20, 2026

(54) METHOD FOR PRODUCING EASILY POLYMERIZABLE COMPOUND

(71) Applicant: NIPPON SHOKUBAI CO., LTD., Osaka (JP)

(72) Inventors: Yuki Kase, Hyogo (JP); Takashi Sugimoto, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 984 days.

(21) Appl. No.: 17/928,754

(22) PCT Filed: May 31, 2021

(86) PCT No.: PCT/JP2021/020632
§ 371 (c)(1),
(2) Date: Nov. 30, 2022

(87) PCT Pub. No.: WO2021/246355
PCT Pub. Date: Dec. 9, 2021

(65) Prior Publication Data
US 2023/0250045 A1 Aug. 10, 2023

(30) Foreign Application Priority Data
Jun. 5, 2020 (JP) ................................ 2020-098798
Jun. 5, 2020 (JP) ................................ 2020-098800

(51) Int. Cl.
*C07C 51/44* (2006.01)
*C07C 67/54* (2006.01)

(52) U.S. Cl.
CPC .............. *C07C 51/44* (2013.01); *C07C 67/54* (2013.01)

(58) Field of Classification Search
None
See application file for complete search history.

(56) References Cited

U.S. PATENT DOCUMENTS 6,348,135 B1 * 2/2002 Nakahara ................ C07C 67/54 203/DIG. 21
6,409,886 B1 6/2002 Matsumoto et al.
(Continued)

FOREIGN PATENT DOCUMENTS

CN 1267660 9/2000
CN 1268384 10/2000
(Continued)

OTHER PUBLICATIONS

Machine translation of Ogawa (JP2014162783, published on Sep. 8, 2014), obtained Nov. 2025 (Year: 2025).*
(Continued)

*Primary Examiner* — Amy C Bonaparte
(74) *Attorney, Agent, or Firm* — Wenderoth, Lind & Ponack, L.L.P.

(57) ABSTRACT

A method for producing an easily polymerizable compound, comprising a step of introducing an easily polymerizable compound-containing liquid into a vaporization separation column (1) selected from a distillation column and a stripping column to purify, wherein: the vaporization separation column (1) is provided with a circulation path (2) for returning a drawn liquid, obtained by withdrawing at least a part of a bottom liquid (3) of the column, to the vaporization separation column (1); the circulation path (2) is provided with a reboiler (4) having a heating part (5) and a supply port (7) for supplying an oxygen-containing gas on an upstream side of the reboiler (4); the supply port (7) is located below an inlet of the heating part (5) with a height difference of 0.5 m or more; and an oxygen-containing gas is supplied to the drawn liquid from the supply port (7).

12 Claims, 2 Drawing Sheets

(56) References Cited

U.S. PATENT DOCUMENTS

| | | | | |
|---|---|---|---|---|
| 6,596,129 | B1 | 7/2003 | Yoneda et al. | |
| 6,641,700 | B1 | 11/2003 | Matsumoto et al. | |
| 6,666,956 | B1 | 12/2003 | Nishimura et al. | |
| 2002/0008064 | A1 | 1/2002 | Hamamoto et al. | |
| 2004/0225151 | A1 | 11/2004 | Yada et al. | |
| 2006/0142613 | A1 | 6/2006 | Yada et al. | |
| 2006/0249365 | A1 | 11/2006 | Yada et al. | |
| 2008/0197086 | A1* | 8/2008 | Mosler | C08F 20/06 261/155 |

FOREIGN PATENT DOCUMENTS

| | | |
|---|---|---|
| CN | 1270950 | 10/2000 |
| CN | 1295058 | 5/2001 |
| CN | 1564799 | 1/2005 |
| CN | 1697676 | 11/2005 |
| JP | 2000-239229 | 9/2000 |
| JP | 2000-256258 | 9/2000 |
| JP | 2002-001017 | 1/2002 |
| JP | 2008-546531 | 12/2008 |
| JP | 2013-212995 | 10/2013 |
| JP | 2014-162783 | 9/2014 |
| JP | 2018-115155 | 7/2018 |

OTHER PUBLICATIONS

Extended European Search Report issued Jun. 11, 2024 in European Patent Application No. 21818506.4.

International Search Report issued Aug. 10, 2021 in International (PCT) Application No. PCT/JP2021/020632.

Office Action issued Aug. 20, 2025 in corresponding Indian Patent Application No. 202247073838.

Communication pursuant to Rule 114(2) EPC issued Apr. 30, 2024, in corresponding European Patent Application No. 21818506.4.

Japanese Office Action dated Jun. 4, 2024, in corresponding Japanese Patent Application No. 2020-098798, with English language translation.

Notice of Submission by Publications issued Nov. 21, 2023 in corresponding Japanese Patent Application No. 2020-098798, with English translation.

Shiro Takahashi et al., "Thermal Mixing Characteristics of Two Fluid Flows with Different Temperatures in a T-tube (Mixing Characteristics in a T-tube and Effect of a Downstream Bent Tube)", Proceedings of the JSME, Edition B, vol. 63, No. 613, 1997-1999, pp. 68-74, with English abstract and cited in CA.

Hideaki Obana, "Heat Exchanger Design Handbook" Revised and Enlarged Edition, Second Edition, Kougakutosho Ltd., Nov. 25, 2000, pp. 542, with English translation and cited in CA.

Dioxins Control Office, General Affairs Division, Environmental Management Bureau, Ministry of the Environment, Government of Japan, "Dioxin Behavior Model Handbook", Mar. 2004, 8.1.3. Henry's Constant, with English translation and cited in CA.

Xiang Liu et al., "Thermally Induced Aerobic Autopolymerization of Methyl Methacrylate in Amide-Type Solvents: Simultaneous Polymerization during Induction via Direct In Situ $O_2$ Activation", Macromolecular Chemistry and Physics, 2015, vol. 216, pp. 1201-1211.

Office Action issued Sep. 15, 2025 in corresponding European Patent Application No. 21 818 506.4.

Office Action issued Dec. 30, 2024 in corresponding Indonesian Patent Application No. P00202215851, with machine English translation.

Acrylic acid, Health and Safety Guide, No. 104, 1997, World Health Organization/International Labour Organisation International Programme on Chemical Safety (IPCS), pp. 1-11.

* cited by examiner

[Fig. 1]
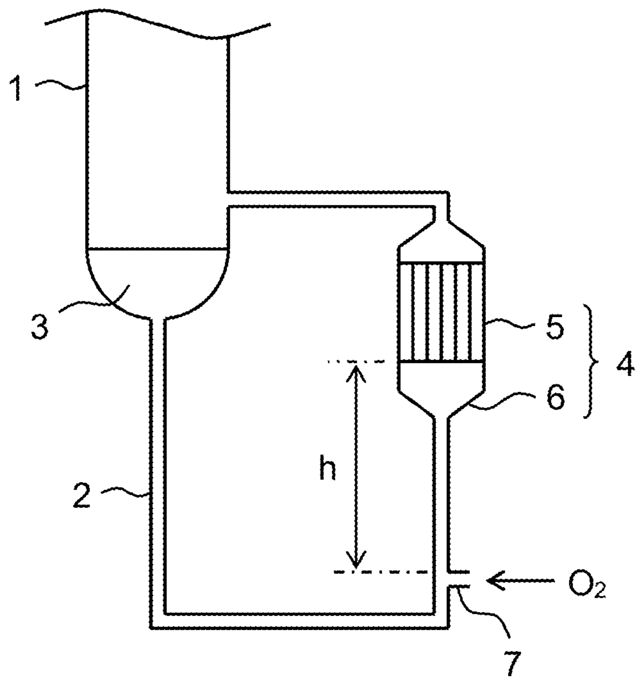

[Fig. 2]
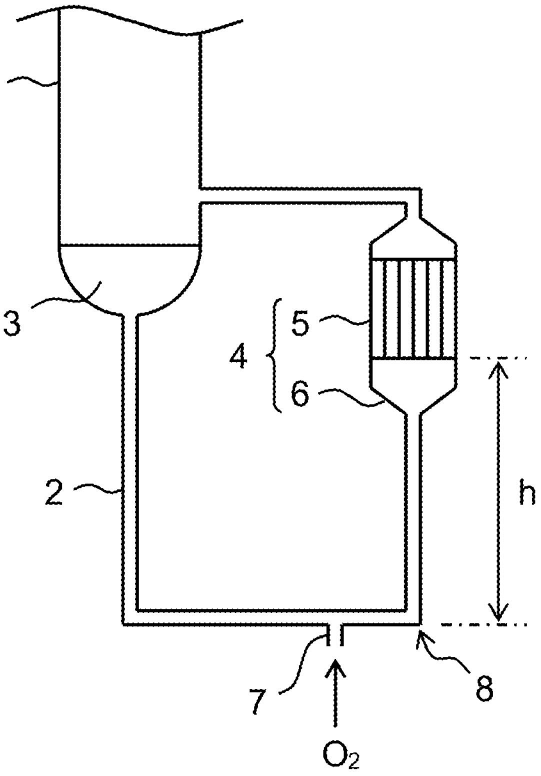

METHOD FOR PRODUCING EASILY POLYMERIZABLE COMPOUND

TECHNICAL FIELD

The present invention relates to a method for producing an easily polymerizable compound, including a step of purifying an easily polymerizable compound such as (meth) acrylic acid or (meth)acrylic acid ester by distillation.

BACKGROUND ART

Conventionally, a method for purifying an easily polymerizable compound such as (meth)acrylic acid and (meth) acrylic acid ester using a vaporization separation column such as a distillation column is known. The vaporization separation column may be provided with a circulation path that at least a part of a bottom liquid of the column is withdrawn, heated in a reboiler, and returned to the vaporization separation column. Since a easily polymerizable substance is easily polymerized, polymerization is occur in a production process, which may force stoppage of the equipment, and various measures to prevent polymerization have been examined.

For example, Patent Literature 1 discloses a method of distilling an easily polymerizable compound or an easily polymerizable compound-containing liquid, in which an easily polymerizable compound or an easily polymerizable compound-containing liquid is distilled by using a distillation column equipped with a reboiler, and a liquid level in the distillation column is maintained within a predetermined range using the reboiler having a predetermined dimension. Patent Literature 2 discloses a method for producing (meth) acrylic acid or its ester, comprising a step of introducing a process liquid containing (meth)acrylic acid or its ester into a distillation column to distill, wherein the distillation column is provided with a bottom liquid circulation line equipped with a reboiler, a part of the process liquid is withdrawn from a stream of the process liquid, the withdrawn liquid and an oxygen-containing gas are mixed in a static mixer to generate a gas-liquid mixed flow, and the gas-liquid mixed flow is fed to the distillation column.

CITATION LIST

Patent Literature

Patent Literature 1
Japanese Unexamined Patent Application Publication No. 2000-239229
Patent Literature 2
Japanese Unexamined Patent Application Publication No. 2014-162783

SUMMARY OF INVENTION

Technical Problem

As disclosed in Patent Literatures 1 and 2, when purifying an easily polymerizable compound-containing liquid using a vaporization separation column having a circulation path with a reboiler, a drawn liquid obtained by withdrawing at least a part of a bottom liquid of the vaporization separation column is heated in the reboiler of the circulation path (specifically, a heating part of the reboiler) and polymerization reaction of the easily polymerizable compound is likely to proceed, and thus, measures to prevent polymerization come to be particularly important.

The present invention has been made in view of the above circumstances, and an object of the present invention is to provide a method for producing an easily polymerizable compound comprising a step of purifying an easily polymerizable compound by using an evaporation separation column provided with a circulation path having a heating part, which can suppress polymerization of the easily polymerizable compound in the heating part.

Solution to Problem

The present invention includes the following inventions.

[1] A method for producing an easily polymerizable compound, comprising a step of introducing an easily polymerizable compound-containing liquid into a vaporization separation column selected from a distillation column and a stripping column to purify, wherein:

the vaporization separation column is provided with a circulation path for returning a drawn liquid, obtained by withdrawing at least a part of a bottom liquid of the column, to the vaporization separation column;

the circulation path is provided with a supply port for supplying an oxygen-containing gas and a reboiler having a heating part in order from an upstream side;

the supply port is located below an inlet of the heating part with a height difference of 0.5 m or more; and an oxygen-containing gas is supplied to the drawn liquid from the supply port.

[2] The method for producing an easily polymerizable compound according to [1], wherein the easily polymerizable compound-containing liquid is introduced into the vaporization separation column and purified under reduced pressure.

[3] The method for producing an easily polymerizable compound according to [1], wherein the easily polymerizable compound-containing liquid is introduced into the vaporization separation column and purified under normal pressure or increased pressure.

[4] The method for producing an easily polymerizable compound according to any one of [1] to [3], wherein a pressure of the withdrawn liquid at the supply port is 30 kPa or more higher than a gas pressure on an upper surface of the bottom liquid.

[5] The method for producing an easily polymerizable compound according to any one of [1] to [4], wherein an average retention time of the drawn liquid from the supply port of the circulation path to the inlet of the heating part is 2 seconds or longer.

[6] The method for producing an easily polymerizable compound according to any one of [1] to [5], wherein the circulation path has a bent portion between the supply port and the heating part.

[7] The method for producing an easily polymerizable compound according to any one of [1] to [6], wherein the supply port is provided in a horizontal portion where the circulation path extends substantial horizontally.

[8] The method for producing an easily polymerizable compound according to [7], wherein an average retention time of the drawn liquid in the horizontal portion is 0.5 seconds or longer.

[9] The method for producing an easily polymerizable compound according to any one of [1] to [8], wherein a widened portion is provided at a connection between the circulation path on an upstream side of the heating part and the heating part.

[10] The method for producing an easily polymerizable compound according to any one of [1] to [9], wherein the reboiler having the heating part is composed of a plate heat exchanger, a shell-and-tube heat exchanger, a double-tube heat exchanger, a coil heat exchanger, or a spiral heat exchanger.

[11] The method for producing an easily polymerizable compound according to any one of [1] to [10], wherein the oxygen-containing gas is supplied as microbubbles.

[12] The method for producing an easily polymerizable compound according to any one of [1] to [11], wherein the easily polymerizable compound is (meth)acrylic acid or (meth)acrylic acid ester.

Advantageous Effects of Invention

In the method for producing an easily polymerizable compound of the present invention, an easily polymerizable compound-containing liquid is purified using a vaporization separation column, and a supply port for an oxygen-containing gas is provided on an upstream side of a reboiler in a drawn liquid circulation path of the vaporization separation column, at a position below an inlet of a heating part of the reboiler with a height difference of 0.5 m or more. Thereby, the oxygen-containing gas is able to be supplied to the circulating liquid under a higher pressure condition, and it is possible to quickly dissolve the supplied oxygen into the circulating liquid or to dissolve more amount of oxygen into the circulating liquid. As a result, a polymerization-inhibiting effect in the circulation path is enhanced, and polymerization of the easily polymerizable compound can be suppressed especially in the heating part of the reboiler where polymerization reaction easily occurs.

BRIEF DESCRIPTION OF THE DRAWINGS

FIG. 1 shows an example of a system configuration around a vaporization separation column used in a method for producing an easily polymerizable compound of the present invention.

FIG. 2 shows another example of a system configuration around a vaporization separation column used in a method for producing an easily polymerizable compound of the present invention.

DESCRIPTION OF THE PREFERRED EMBODIMENTS

A method for producing an easily polymerizable compound of the present invention comprises a step of introducing an easily polymerizable compound-containing liquid into a vaporization separation column selected from a distillation column and a stripping column to purify. By introducing an easily polymerizable compound-containing liquid into a vaporization separation column and purifying it, at least a part of the components having a lower and/or higher boiling point than the easily polymerizable compound is removed from the easily polymerizable compound-containing liquid, thereby obtaining a purified easily polymerizable compound. Hereinafter, the step of introducing the easily polymerizable compound-containing liquid into the vaporization separation column to purify is referred to as a "vaporization separation step".

The easily polymerizable compound is not particularly limited as long as it is easily polymerized when heated in the vaporization separation column, and examples thereof include (meth)acrylic acid and its ester, maleic anhydride and its ester, acrylonitrile, styrene, divinyl benzene, vinyl toluene, diethylene glycol monovinyl ether, and others. Among them, typical easily polymerizable compounds include (meth)acrylic acid and its esters. Examples of (meth)acrylic acid ester include, for example, methyl (meth)acrylate, ethyl (meth)acrylate, butyl (meth)acrylate, isobutyl (meth)acrylate, t-butyl (meth)acrylate, 2-ethylhexyl (meth)acrylate, nonyl (meth)acrylate, 2-hydroxyethyl (meth)acrylate, 2-hydroxypropyl (meth)acrylate, ethylene glycol di(meth)acrylate, polyethylene glycol di(meth)acrylate, trimethylolpropane di(meth)acrylate, trimethylolpropane tri(meth)acrylate, 2-(2-vinyloxyethoxy)ethyl (meth)acrylate, methoxyethyl (meth)acrylate, benzyl (meth)acrylate, glycidyl (meth)acrylate, and others. For example, in the case of conducting the vaporization separation step under reduced pressure, preferable examples of the easily polymerizable compound include (meth)acrylic acid, butyl (meth)acrylate, isobutyl (meth)acrylate, t-butyl (meth)acrylate, 2-ethylhexyl (meth)acrylate, 2-hydroxyethyl (meth)acrylate, 2-hydroxypropyl (meth)acrylate, methoxyethyl (meth)acrylate, nonyl (meth)acrylate, ethylene glycol di(meth)acrylate, polyethylene glycol di(meth)acrylate, trimethylolpropane di(meth)acrylate, trimethylolpropane tri(meth)acrylate, 2-(2-vinyloxyethoxy)ethyl (meth)acrylate, benzyl (meth)acrylate and glycidyl (meth)acrylate, and in the case of conducting the vaporization separation step under normal pressure or increased pressure, preferable examples of the easily polymerizable compound include maleic anhydride, acrylonitrile, styrene, vinyl toluene, methyl (meth)acrylate and ethyl (meth)acrylate.

The easily polymerizable compound-containing liquid introduced into the vaporization separation column of the distillation column or the stripping column is not particularly limited as long as it is a liquid obtained in an easily polymerizable compound production process and contains an easily polymerizable compound. For example, in the case where the easily polymerizable compound is (meth)acrylic acid, examples of the easily polymerizable compound-containing liquid include a (meth)acrylic acid-containing liquid obtained in a collection step or a condensation step preceding the vaporization separation step (specifically, a (meth)acrylic acid-containing liquid obtained by recovering a (meth)acrylic acid-containing gas with a liquid), a (meth)acrylic acid-containing liquid obtained in any purification step preceding the vaporization separation step, a purification residue obtained in any purification step subsequent to the vaporization separation step, and the like. Purification means that can be used in any of these purification steps include crystallization, distillation (fractional distillation), stripping, extraction and the like, which may be combined.

Easily polymerizable compound concentration in the easily polymerizable compound-containing liquid introduced into the vaporization separation column in the vaporization separation step is not particularly limited, and from the viewpoint that the effect of the present invention can be exerted more remarkably, the easily polymerizable compound concentration in the easily polymerizable compound-containing liquid is preferably, for example, 50 mass % or more, more preferably 60 mass % or more, even more preferably 70 mass % or more, still even more preferably 80 mass % or more, and particularly preferably 90 mass % or more. The upper limit of the easily polymerizable compound concentration in the easily polymerizable compound-containing liquid is not particularly limited, and for example, it may be 97 mass % or less.

As the distillation column or the stripping column used as the vaporization separation column, a tower-type equipment such as a tray column in which trays (sieve trays) are provided in the column (e.g., a perforated plate column and a bubble cap column) and a packed column filled with a packing in the column is preferably used. The vaporization separation column has a top part, a middle part and a bottom part, and provided that the vaporization separation column is divided in a height direction, the range, with respect to the height direction, in which the tray or the packing is provided is referred to as the middle part, a top side thereto is referred to as the top part, and a bottom side thereto is referred to as the bottom part.

An introducing position of the easily polymerizable compound-containing liquid into the vaporization separation column and a withdrawing position of a purified easily polymerizable compound withdrawn from the vaporization separation column may be appropriately set, according to the composition of the easily polymerizable compound-containing liquid and the type of the vaporization separation column, that is, depending on whether the vaporization separation column is a distillation column or a stripping column.

In the case where the vaporization separation column is a distillation column, it is preferable that the easily polymerizable compound-containing liquid is introduced into the distillation column from the middle part of the distillation column. The withdrawing position of the purified easily polymerizable compound withdrawn from the distillation column may be appropriately set according to the composition of the easily polymerizable compound-containing liquid introduced into the distillation column. For example, in the case where a (meth)acrylic acid-containing liquid is introduced into the distillation column and purified, it is preferable that the purified (meth)acrylic acid is withdrawn from the distillation column as follows. In the case where the distillation column is for distilling the (meth)acrylic acid-containing liquid obtained in the preceding collection step or condensation step, since the (meth)acrylic acid-containing liquid contains more amount of components with lower boiling point than (meth)acrylic acid, it is preferable to withdraw purified (meth)acrylic acid from the middle part and/or the bottom part of the distillation column. In this case, the withdrawing position of the purified (meth)acrylic acid is preferably closer to the bottom of the column than the introducing position of the (meth)acrylic acid-containing liquid. On the other hand, in the case where the (meth) acrylic acid-containing liquid contains more amount of components with higher boiling point than (meth)acrylic acid, such as Michael adducts and maleic acid, the purified (meth)acrylic acid is preferably withdrawn from a position closer to a top of the column than the introducing position of the (meth)acrylic acid-containing liquid, and more preferably withdrawn from the top part of the column. In this case, the purified (meth)acrylic acid is preferably withdrawn as vapor.

In the case of withdrawing the purified (meth)acrylic acid from the middle part of the column, the purified (meth) acrylic acid may be withdrawn as a liquid or as a vapor. For withdrawing the purified (meth)acrylic acid from the middle part of the column as a liquid, an outlet port may be provided at a position where the shelf is provided or a chimney or the like may be provided to the shelf, for example in a tray column. When the purified (meth)acrylic acid is withdrawn as a liquid, the purified (meth)acrylic acid can be supplied to the subsequent step without additional processing such as condensation. In the case of withdrawing the purified (meth) acrylic acid as a vapor, the purified (meth)acrylic acid with a relatively low content of impurities is easily obtained. In the distillation column, a reflux liquid flows down from the top to the bottom of the column and a part of the reflux liquid remains on the shelf, and therefore, by providing the outlet port at a position sufficiently above the shelf, it becomes easy to preferentially withdraw the purified (meth)acrylic acid in the form of vapor while suppressing discharge of the reflux liquid.

In the case of withdrawing the purified (meth)acrylic acid from the bottom part of the column, a path for withdrawing the purified (meth)acrylic acid may be connected to a drawn liquid circulation path described below and the purified (meth)acrylic acid may be withdrawn from that path, or a path for withdrawing the purified (meth)acrylic acid may be connected directly to the bottom part of the distillation column, separately from the drawn liquid circulation path. In this case, the purified (meth)acrylic acid is preferably withdrawn as a liquid.

In the case where the vaporization separation column is a stripping column, it is preferable that the easily polymerizable compound-containing liquid is introduced into the stripping column from the middle part or the top part of the column and the purified easily polymerizable compound is withdrawn from the bottom part of the column. Basically In the stripping column, a stripping gas is supplied from the bottom part of the column, low boiling point components contained in the easily polymerizable compound-containing liquid are vaporized to be separated. The purified easily polymerizable compound is preferably withdrawn from the stripping column as a liquid, and in this case, a path for withdrawing a purified easily polymerizable compound-containing liquid may be provided to a drawn liquid circulation path described below, or a path for withdrawing the purified easily polymerizable compound-containing liquid may be connected directly to the bottom part of the striping column, separately from the drawn liquid circulation path.

The vaporization separation column is provided with a drawn liquid circulation path for returning a drawn liquid that is obtained by withdrawing at least a part of a bottom liquid accumulated at the bottom part of the column to the vaporization separation column. The drawn liquid circulation path is provided with a reboiler having a heating part. The drawn liquid circulation path is a means for increasing temperature in the vaporization separation column and facilitating its temperature control to improve separation efficiency in the vaporization separation column, by heating the dawn liquid withdrawn from the bottom part of the column with the reboiler and returning it to the vaporization separation column. Therefore, as long as this purpose can be achieved, the type of connection between the vaporization separation column and the drawn liquid circulation path and the structure of the drawn liquid circulation path are not particularly limited. However, a liquid level gauge or the like, that can not achieve the above purpose, is not referred to as the drawn liquid circulation path in the present invention.

As for the drawn liquid circulation path, one drawn liquid circulation path may be provided for one vaporization separation column, a plurality of drawn liquid circulation paths may be provided for one vaporization separation column, or one drawn liquid circulation path may be provided for a plurality of vaporization separation columns. In the case where one drawn liquid circulation path is provided for a plurality of vaporization separation columns, the drawn liquids of the plurality of vaporization separation columns may be collected to be heated and then returned to the respective vaporization separation columns. From the viewpoint of increasing separation efficiency in the vaporization separation column and enabling more precise control, it is preferable that a plurality of drawn liquid circulation paths are provided for one vaporization separation column. Nevertheless, as long as the required accuracy can be obtained, it is convenient and preferable that one drawn liquid circulation path is provided for one vaporization separation column.

The circulation path is preferably provided so as to return the bottom liquid withdrawn from the bottom part of the column to the bottom part of the column. Thereby, temperature control in the vaporization separation column is facilitated. A returning position of the circulation path of the bottom liquid to the bottom part of the column may be higher than or lower than the position at which the bottom liquid is withdrawn from the bottom part of the column, or may be at the same height as that. In the following, the drawn liquid flowing through the circulation path may be referred to as a "circulating liquid".

As the reboiler, a heat exchanger having a heat transfer surface is preferably used, which facilitates temperature control of the circulating liquid. In this case, the heat transfer surface comes to be the heating part of the reboiler. As the heat exchanger, a conventionally known heat exchanger can be used, and for example, a plate heat exchanger comprising a single plate or a plurality of plates stacked at intervals, wherein a medium-present part(s) and a circulating liquid-present part(s) are alternately disposed while being separated by the plate(s); a multitubular (shell-and-tube) heat exchanger comprising a plurality of tubes in a vessel, wherein heat is exchanged between the interiors and exteriors of the tubes; a double-tube heat exchanger comprising an outer tube and an inner tube disposed in the outer tube, wherein heat is exchanged between the interior and exterior of the inner tube; a coil heat exchanger comprising one coil-shaped tube disposed in a vessel, wherein heat is exchanged between the interior and exterior of the tube; a spiral plate exchanger comprising a center tube whose cross-section is divided into two parts and two heat exchanger plates winding the center tube in whorl, whereby two whorl-like paths are formed; or the like may be employed. A cross-sectional shape of the tubes used in the multitubular heat exchanger, the double-tube heat exchanger, the coil heat exchanger and the spiral plate exchanger is not particularly limited. From the viewpoint of heat transfer efficiency and ease of maintenance, a plate heat exchanger and a shell-and-tube heat exchanger in which the circulating liquid flows through tubes are preferable, and the latter is particularly preferable.

The heating part of the reboiler is preferably configured so that the circulating liquid flows vertically upward. As described later, in the present invention, a supply port for an oxygen-containing gas is provided at a position lower than an inlet of the heating part of the reboiler, and therefore, in order to prevent the oxygen-containing gas supplied to the circulating liquid from staying in the heating part or the oxygen-containing gas from flowing unevenly in the heating part, the heating part is preferably configured so that the circulating liquid flows vertically upward. From the same point of view, in the case of using a heat exchanger as the reboiler, it is preferable to adopt a plate heat exchanger or a shell-and-tube heat exchanger. In the case of using a heat exchanger as the reboiler, the inlet of the heating part refers to the most upstream part of the heat transfer surface of the heat exchanger. For example, in the case of a shell-and-tube heat exchanger in which the circulating liquid flows through tubes, a tube plate surface o the upstream side corresponds to the inlet of the heating part.

In the vaporization separation process, it is desired that polymerization of easily polymerizable substances is suppressed. Therefore, it is preferable that the easily polymerizable compound-containing liquid introduced into the vaporization separation column contains a polymerization inhibitor, or the polymerization inhibitor is added in the vaporization separation column. In particular, since temperature at the bottom part of the vaporization separation column is high and polymerization reaction is easily proceed, it is preferable that the bottom liquid contains a polymerization inhibitor.

As the polymerization inhibitor, conventionally known polymerization inhibitors can be used, and examples of the polymerization inhibitor includes, for example, quinone compounds such as hydroquinone and methoquinone (p-methoxyphenol); phenothiazine compounds such as phenothiazine, bis-(α-methylbenzyl)phenothiazine, 3,7-dioctylphenothiazine and bis-(α-dimethylbenzyl)phenothiazine; N-oxyl compounds such as 2,2,6,6-tetramethylpiperidinooxyl, 4-hydroxy-2,2,6,6-tetramethylpiperidinooxyl and 4,4',4"-tris-(2,2,6,6-tetramethylpiperidinooxyl)phosphite; copper salt compounds such as copper dialkyl dithiocarbamate, copper acetate, copper naphthenate, copper acrylate, copper sulfate, copper nitrate and copper chloride; manganese salt compounds such manganese dialkyl dithiocarbamate, manganese diphenyl dithiocarbamate, manganese formate, manganese acetate, manganese octanoate and manganese naphtenate; nitroso compounds such as N-nitrosophenyl hydroxylamine and its salts, p-nitrosophenol, and N-nitrosodiphenylamine and its salts; and the like. These polymerization inhibitors may be used alone or in combination of two or more. Among them, it is preferable to use at least quinones as the polymerization inhibitor.

Polymerization inhibitor concentration in the bottom liquid may be appropriately set, and from the viewpoint of appropriately exerting the polymerization-inhibiting effect in the vaporization separation column, it is preferably 1 mass ppm or more, and more preferable 10 mass ppm or more, even more preferably 100 mass ppm or more, and particularly preferably 1000 mass ppm or more. The upper limit of the polymerization inhibitor concentration in the bottom liquid is not particularly limited, however, from the viewpoint of reducing the addition amount of the polymerization inhibitor, it is preferably 50000 mass ppm or less, more preferably 10000 mass ppm or less, even more preferably 5000 mass ppm or less, and particularly preferably 2000 mass ppm or less.

In the vaporization separation column, purification of the easily polymerizable compound-containing liquid may be conducted under reduced pressure, normal pressure, or increased pressure. In order to ensure that the easily polymerizable compound-containing liquid is properly separated and purified in the vaporization separation column, pressure in the vaporization separation column is preferably controlled as satisfying the following inequalities: pressure at the bottom part of the column>pressure at the middle part of the column>pressure at the top part of the column.

In the vaporization separation column, temperature tends to increase toward the bottom side of the column, and particularly in the reboiler in the drawn liquid circulation path, the drawn liquid is heated and polymerization reaction of the easily polymerizable compound is likely to proceed, it is important to take measures to prevent polymerization of the easily polymerizable compound. When the polymerization reaction of the easily polymerizable compound proceeds in the heating part of the reboiler, polymer adheres and deposits on the heating part, which may cause clogging of a flow path in the heating part.

Therefore, a supply port for supplying an oxygen-containing gas is provided on the upstream side of the reboiler in the circulation path, and an oxygen-containing gas is supplied from the supply port to the drawn liquid (circulating liquid) flowing in the circulation path. As a result, polymerization-inhibiting effect in the circulation path is enhanced, and polymerization of the easily polymerizable compound can be suppressed especially in the heating part of the reboiler where polymerization reaction easily occurs. As the oxygen-containing gas, pure oxygen gas, air, a gas obtained by mixing nitrogen, oxygen and air, having any oxygen concentration, a process waste gas, or the like can be used.

When supplying the oxygen-containing gas to the circulating liquid to suppress polymerization in the heating part of the reboiler as described above, it is desirable that as much of the supplied oxygen is dissolved into the circulating liquid as possible before the oxygen-containing gas supplied to the circulating liquid reaches the heating part of the reboiler. For that, it is desirable the oxygen-containing gas is supplied to the circulating liquid under as high a pressure as possible. Therefore, in the present invention, the oxygen-containing gas is supplied upstream of the reboiler at a high liquid pressure point where oxygen saturation concentration in the circulating liquid can be made high. The supply port for the oxygen-containing gas is provided in the circulation path and located below the inlet of the heating part of the reboiler with a height difference of 0.5 m or more, thereby making more amount of oxygen to be dissolved in the circulating liquid. This is described with reference to the drawings.

FIGS. 1 and 2 show schematic diagrams of a system configuration around the vaporization separation column. In a vaporization separation column 1, purification of an easily polymerizable compound-containing liquid is conducted. The vaporization separation column 1 is provided with a circulation path 2 for withdrawing at least a part of a bottom liquid 3 and returning it to the vaporization separation column 1, and the circulation path 2 is provided with a reboiler 4 having a heating part 5 and a supply port 7 for supplying an oxygen-containing gas provided upstream the heating part 5 and located below the heating part 5. The supply port 7 for the oxygen-containing gas is located below an inlet of the heating part 5 of the reboiler 4 with a height difference of 0.5 m or more, whereby the oxygen-containing gas is able to be supplied to the circulating liquid under a higher pressure. In the drawings, the arrow h indicates the height difference between the inlet of the heating part 5 of the reboiler 4 and the supply port 7 for the oxygen-containing gas. By providing the supply port 7 for the oxygen-containing gas at such a position, it is possible to quickly dissolve the supplied oxygen into the circulating liquid or to dissolve more amount of oxygen into the circulating liquid. In this case, 5 kPa or more of liquid head pressure difference between the supply port 7 for the oxygen-containing gas and the inlet of the heating part 5 of the reboiler 4 is applied to the supply port 7 for the oxygen-containing gas, in addition to a liquid head pressure at the inlet of the heating part 5 of the reboiler 4, and therefore, the oxygen-containing gas is able to be supplied under a higher pressure. Further, it is possible to ensure sufficient time for the supplied oxygen to dissolve in the circulating liquid until the oxygen-containing gas supplied to the circulating liquid from the supply port 7 reaches the heating part 5 of the reboiler 4. By supplying the oxygen-containing gas to the circulating liquid in this manner, polymerization reaction of the easily polymerizable compound can be suppressed in the heating part 5, and uneven polymerization-inhibiting effect in the heating part 5 can also be suppressed due to dissolution of the supplied oxygen into the circulating liquid.

In the case of providing the supply port 7 for the oxygen-containing gas in the circulation path 2 as described above, different effects can be obtained depending on the pressure conditions when the easily polymerizable compound-containing liquid is purified in the vaporization separation column 1. For example, in the case where the easily polymerizable compound-containing liquid is purified in the vaporization separation column 1 under reduced pressure, the temperature required for vaporization and separation is able to be set low, which also makes it possible to suppress polymerization of the easily polymerizable compound also in the vaporization separation column 1. That is, since a gas pressure on an upper surface of the bottom liquid 3 in the vaporization separation column 1 comes to be less than normal pressure, vaporization temperature of the easily polymerizable compound-containing liquid can be lowered, and polymerization of the easily polymerizable compound in the vaporization separation column 1 can be suppressed. Meanwhile, in this case, saturation concentration of a gas dissolved in the bottom liquid 3 becomes lowered, and the bottom liquid 3 may contain less amount of oxygen that has polymerization-inhibiting effect; however, since the supply port 7 for the oxygen-containing gas is provided at a position below the inlet of the heating part 5 of the reboiler 4 with a height difference of 0.5 m or more, the oxygen-containing gas is supplied to the circulating liquid under a higher pressure, and polymerization reaction of the easily polymerizable compound in the heating part 5 of the reboiler 4 can be suppressed.

In the above case, pressure at the bottom part of the vaporization separation column 1, that is, the gas pressure (absolute pressure) on the upper surface of the bottom liquid, may be set as appropriate, depending on temperature dependence or a temperature-vapor pressure correlation of the polymerization reaction of the easily polymerizable compound or its containing composition in the vaporization separation column, and it is usually, for example, preferably 50 kPa or lower, more preferably 40 kPa or lower, and even more preferably 30 kPa or lower. By setting the gas pressure on the upper surface of the bottom liquid to 50 kPa or lower, the temperature required for vaporizing the easily polymerizable compound can be lowered. The lower limit of the gas pressure on the upper surface of the bottom liquid may be appropriately set in consideration of a cost for reducing the pressure and durability of the vaporization separation column, and it is usually, for example, preferably 5 kPa or higher, more preferably 8 kPa or higher, and even more preferably 10 kPa or higher.

On the other hand, when the easily polymerizable compound-containing liquid is purified in the vaporization separation column 1 under normal pressure or increased pressure, the gas pressure on the upper surface of the bottom liquid 3 comes to be normal pressure or higher in the vaporization separation column 1, and a pressure higher than normal pressure can be applied to the liquid surface of the bottom liquid. In this case, 5 kPa or more of the liquid head pressure difference between the supply port 7 for the oxygen-containing gas and the inlet of the heating part 5 of the reboiler 4 is applied to the supply port 7 for the oxygen-containing gas, in addition to the gas pressure on the upper surface of the bottom liquid 3 and liquid head difference between the liquid surface of the bottom liquid 3 and the inlet of the heating part 5 of the reboiler 4, and hence, the oxygen-containing gas is able to be supplied under a higher pressure. Therefore, it is possible to quickly dissolve the supplied oxygen in the circulating liquid, or to dissolve more amount of oxygen in the circulating liquid. In this case, in the vaporization separation column 1, it is more preferable to purify the easily polymerizable compound-containing liquid under increased pressure.

In the above case, the pressure at the bottom part of the vaporization separation column 1, that is, the gas pressure (absolute pressure) on the upper surface of the bottom liquid, may be set as appropriate, depending on temperature dependence or a temperature-vapor pressure correlation of the polymerization reaction of the easily polymerizable compound or its containing composition in the vaporization separation column, and it is preferably 100 kPa or higher, more preferably 105 kPa or higher, and even more preferably 120 kPa or higher. By setting the gas pressure on the upper surface of the bottom liquid in this manner, it becomes easier to dissolve more amount of the oxygen-containing gas into the circulating liquid. From the viewpoint of preventing the temperature required for vaporization and separation in the vaporization separation column from becoming too high and suppressing polymerization of the easily polymerizable compound in the vaporization separation column, the upper limit of the gas pressure on the upper surface of the bottom liquid is preferably, for example, 250 kPa or lower, more preferably 200 kPa or lower, and even more preferably 150 kPa or lower.

From the viewpoint of supplying the oxygen-containing gas to the circulating liquid under a higher pressure, the position of the supply port 7 in the circulation path 2 is located below the inlet of the heating part 5 of the reboiler 4 with a height difference of preferably 1.0 m or more, and more preferably 1.5 m or more. The upper limit of that is not particularly limited, and considering the realistic installation embodiments of the vaporization separation column 1 and the reboiler 4, the height difference is preferably 8.0 m or less, more preferably 6.0 m or less, and even more preferably 4.0 m or less.

The pressure of the circulating liquid (drawn liquid) at the supply port 7 is preferably 30 kPa or more higher, more preferably 40 kPa or more higher, and even more preferably 50 kPa or more higher than the gas pressure on the upper surface of the bottom liquid of the vaporization separation column 1. Thereby, polymerization of the easily polymerizable compound in the reboiler 4 can be suppressed more effectively. The upper limit of the pressure difference between the pressure of the circulating liquid at the supply port 7 and the gas pressure on the upper surface of the bottom liquid of the vaporization separation column 1 is not particularly limited, and considering the realistic installation embodiments of the vaporization separation column 1 and the reboiler 4, the pressure difference is preferably 100 kPa or lower, more preferably 90 kPa or lower, and even more preferably 80 kPa or lower. The pressure of the circulating liquid at the supply port 7 means a pressure in the state where it is not affected by the oxygen-containing gas supplied from the supply port 7, and can be obtained, for example, by measuring a pressure of the circulating liquid at the supply port 7 with no oxygen-containing gas being supplied from the supply port 7. Alternatively, the pressure of the circulating liquid at the supply port 7 may be obtained by measuring a pressure of the circulating liquid at a position distant from the supply port 7 and correcting the obtained pressure value by a pressure drop from the supply port 7 to the measurement position calculated based on a piping configuration of the circulation path 2, a flow velocity of the circulating liquid and others.

Only one supply port 7 may be provided in the circulation path 2, or a plurality of supply ports 7 may be provided in the circulation path 2. In the case of providing a plurality of supply ports 7, it is preferable that the pressure difference between the pressure of the circulating liquid at the at least one supply port and the gas pressure on the upper surface of the bottom liquid is within the above range. Furthermore, the amount of the oxygen-containing gas supplied from the supply port located at the position of the above pressure difference is preferably 50% or more, more preferably 70% or more, even more preferably 80% or more of the total amount of the oxygen-containing gas supplied from all the supply ports. Particularly preferably, the pressure differences between the pressure of the circulating liquid at all the supply ports and the gas pressure on the upper surface of the bottom liquid are within the above range.

A flow rate of the circulating liquid in the circulation path 2 may be set arbitrarily; however, when the Reynolds number in the circulation path 2 is high, the circulating liquid comes to be in a turbulent state and the oxygen-containing gas dissolves faster, and therefore, the Reynolds number of the circulating liquid is preferably 2300 or more. The Reynolds number of the circulating liquid is more preferably 5000 or more, even more preferably 10000 or more, still even more preferably 50000 or more, and particularly preferably 100000 or more.

Examples of a method for flowing the drawn liquid in an intended direction in the circulation path include a self-circulation method using the principle of a thermosiphon and a forced circulation method using a liquid transfer pump. In the latter method, when the supply port 7 is provided on the downstream side (discharge side) of the liquid transfer pump, a discharge pressure of the liquid transfer pump allows the oxygen-containing gas to be fed to the circulating liquid under a higher pressure. On the other hand, when the supply port 7 is provided on the upstream side (suction side) of the liquid feed pump, dissolution of oxygen can be promoted by agitation in the pump. Here, if an excessive amount of the oxygen-containing gas is supplied on the suction side of the liquid transfer pump, cavitation may occur and the pumped volume may be unstable, and therefore, in this case, it is preferable to adjust the supply amount of the oxygen-containing gas appropriately. The supply port 7 may be provided on both the upstream and downstream sides of the liquid transfer pump. The suction side of the liquid transfer pump is connected to the bottom part of the vaporization separation column 1, and the bottom liquid is withdrawn by the liquid transfer pump, heated by the reboiler 4, and then returned to the bottom part of the column.

An average retention time of the circulating liquid (drawn liquid) from the supply port 7 of the circulation path 2 to the inlet of the heating part 5 of the reboiler 4 is preferably 2 seconds or longer, more preferably 3 seconds or longer, and even more preferably 4 seconds or longer. Thereby, the supplied oxygen can be easily fully dissolved into the circulating liquid until the oxygen-containing gas supplied to the circulating liquid reaches the heating part 5 of the reboiler 4. The upper limit of the average retention time is not particularly limited, however, since there is no particular need to install the circulation path 2 excessively long, it may be, for example, 60 seconds or shorter, 30 seconds or shorter, or 15 seconds or shorter. The average retention time of the circulating liquid from the supply port of the oxygen-containing gas of the circulation path to the inlet of the heating part of the reboiler can be obtained by dividing the volume ($m^3$) from the supply port of the oxygen-containing gas of the circulation path to the inlet of the heating part of the reboiler by the flow rate ($m^3$/sec) of the circulating liquid flowing through the circulation path The average retention time can be appropriately adjusted by adjusting the position of the supply port or changing a diameter of the circulation path.

The supply port 7 may be provided in a portion of the circulation path 2 that extends upward (for example, vertically upward or diagonally upward) as shown in FIG. 1, or in a horizontal portion of the circulation path 2 that extends horizontally, as shown in FIG. 2. Alternatively, the supply port 7 may be provided at a bent portion of the circulation path 2. In the case where a plurality of supply ports 7 are provided, the average retention time from the supply port 7 of the circulation path 2 to the inlet of the heating part 5 of the reboiler 4 is determined based on the supply port that provides 50% or more of the total oxygen supply.

It is preferable that the circulation path 2 has a bent portion between the supply port 7 and the heating part 5 of the reboiler 4. By providing the bent portion in the circulation path 2, the oxygen-containing gas is well mixed with the circulating liquid when the circulating liquid passes through the bent portion, and oxygen is easily dissolved in the circulating liquid. The bent portion may, for example, change a horizontal flow to a vertical flow, or may change a horizontal flow in one direction to a horizontal flow in another direction. In FIG. 2, a bent portion 8 for changing a horizontal flow to a vertical flow is provided between the supply port 7 and the heating part 5 of the reboiler 4.

As the bent portion, a elbow pipe or a bend pipe, so-called, can be used. A bending angle of the bent portion is preferably 40° or larger, more preferably 55° or larger, even more preferably 70° or larger, and preferably 125° or smaller, more preferably 110° or smaller, even more preferably 95° or smaller. The bending angle of the bent portion means the angle difference between the extending direction of the pipe axis on the upstream side and the extending direction of the pipe axis on the downstream side of the bent portion, and in a straight pipe portion, the bending angle is 0°.

From the viewpoint of improving mixing efficiency of the oxygen-containing gas with the circulating liquid, it is preferable that a widened portion 6 is provided at a connection between the circulation path 2 on the upstream side of the heating part 5 of the reboiler 4 and the heating part 5. The widened portion 6 is formed such that the cross-sectional area of a flow path through which the circulating liquid flows increases from the upstream side toward the downstream side, and therefore, when the circulating liquid passes through the widened portion 6, a turbulent flow is formed and the oxygen-containing gas is mixed well with the circulating liquid, which makes it easier for oxygen to dissolve into the circulating liquid. In addition, since a linear velocity of the circulating liquid slows down in the widened portion 6, the effect of increasing the amount of oxygen dissolved in the circulating liquid by longing the retention time from the supply port 7 to the inlet of the heating part 5 is also obtained. Furthermore, even when a part of the oxygen-containing gas supplied to the circulating liquid passes through the widened portion 6 in a gaseous state, the oxygen-containing gas is mixed with the circulating liquid in the widened portion 6, thereby reducing uneven distribution of the oxygen-containing gas in the heating part 5. The widened portion may be provided independently, or a heat exchanger having the widened portion may be used as the reboiler.

In the widened portion 6, the cross-sectional area of the flow path through which the circulating liquid flows preferably increases by 1.2 times or more, more preferably by 1.5 times or more, even more preferably by 2 times or more, and preferably by 50 times or less, more preferably by 30 times or less, even more preferably 20 times or less.

As shown in FIG. 2, it is preferable that the supply port 7 of the oxygen-containing gas is provided in a horizontal portion where the circulation path 2 extends substantial horizontally. For example, in the case of providing the supply port 7 in a portion where the circulation path 2 extends vertically, the oxygen-containing gas may rise regardless of the flow direction of the circulating liquid at that point, which may result in poor flow of the circulating liquid or a shortening the contact time between the oxygen-containing liquid gas and the circulating liquid. However, when the supply port 7 is provided in the horizontal portion of the circulation path 2, the oxygen-containing gas and the circulating liquid can be kept under high pressure for a longer period of time in a state of coexistence, which enables oxygen to be dissolved into the circulating liquid more efficiently. In this case, an average retention time of the circulating liquid in the horizontal portion is preferably 0.5 seconds or longer, more preferably 1 second or longer.

A horizontal portion of the circulation path 2 may be provided in a portion that does not include the supply port 7 between the supply port 7 and the inlet of the heating part 5, and in this case as well, the above-described effect of the horizontal portion can be obtained. A plurality of horizontal portions may be provided between the supply port 7 and the inlet of the heating part 5. Therefore, the total average retention time of the circulating liquid in all horizontal portions from the supply port 7 to the inlet of the heating part 5 is preferably 0.5 seconds or longer, more preferably 1 second or longer.

It is preferable that the circulation path 2 does not have a portion extending downward (including diagonally downward) from the upstream side toward the downstream side between the supply port 7 and the heating part 5 of the reboiler 4. As a result, the oxygen-containing gas easily moves to the reboiler 4 side on the flow of the circulating liquid, and it is less likely to occur that the oxygen-containing gas accumulates in a part of the circulation path 2 to obstruct the flow of the circulating liquid. In the case where the horizontal portion is provided in the circulation path 2, it is preferable that the bent portion 8 is provided on the downstream side of the horizontal portion and the circulation path 2 extends upward (for example, vertically upward or diagonally upward) on the downstream side of the bent portion.

The amount of the oxygen-containing gas supplied to the circulating liquid may be appropriately set according to a dissolved oxygen concentration in the circulating liquid at the inlet of the heating part 5 of the reboiler 4. The dissolved oxygen concentration in the circulating liquid at the inlet of the heating part 5 of the reboiler 4 is preferably, for example, 5 mass ppm or more.

As the supply port 7 for supplying the oxygen-containing gas, a nozzle can be used, for example. As the nozzle, a ring-shaped, cylindrical-shaped, or any other shaped nozzle having one or more holes with a diameter of 0.1 mm to 10 mm can be used, for example. A sintered filter may also be used to increase a bubble surface area of the oxygen-containing gas supplied to the circulating liquid.

The oxygen-containing gas may be supplied to the circulating liquid as microbubbles in order to dissolve oxygen into the circulating liquid more quickly. Since microbubbles have a smaller bubble diameter than normal bubbles, a total surface area of microbubbles is increased under the condition that the amount of oxygen-containing gas to be supplied is the same, and oxygen is more quickly dissolved in the circulating liquid.

The microbubbles may include so-called nanobubbles, and bubbles with a diameter of 0.1 μm to 100 μm when generated are preferably used. A conventionally known microbubble generator can be used. Examples of a method for generating microbubbles include: a gas-liquid two-phase flow swirling method in which water flow or mechanical agitation generates a vortex or shear flow to fragment bubbles (e.g., a swirling flow method, a static mixer method, a mechanical shear (rotation) method); a pressurized dissolution method in which gas is dissolved in a liquid to be treated under increased pressure and then depressurized to regasify the gas dissolved in the liquid to be treated as microbubbles; a venturi method in which gas-liquid fluid flows through a pipe with a throat and the gas bubbles are subdivided by being compressed and decompressed when passing through the throat; a cavitation nozzle method in which a liquid static pressure of a liquid is locally lowered to vaporize a part of the liquid and generate vapor bubbles, and the pressure is recovered in a short time to subdivide the vapor bubbles; a filter method in which gas is passed through a filter with nano-porous in a liquid to be subdivided; and any method can be used.

In the present invention, as the easily polymerizable compound-containing liquid to be subjected to the vaporization separation step, an easily polymerizable compound-containing liquid obtained in the preceding step thereof can be used. For example, in the case where the easily polymerizable compound is (meth)acrylic acid, a (meth)acrylic acid-containing liquid obtained in a collection step, a condensation step, or the like can be used. Hereinafter, a method for obtaining a (meth)acrylic acid-containing liquid to be introduced into the vaporization separation column is described by taking a (meth)acrylic acid production process as an example.

In the case that the easily polymerizable compound is (meth)acrylic acid, the method for producing an easily polymerizable compound of the present invention (in this case, the method for producing (meth)acrylic acid) preferably comprises the steps of: obtaining a (meth)acrylic acid-containing gas by subjecting a (meth)acrylic acid production raw material to a catalytic gas phase oxidation reaction; and obtaining a (meth)acrylic acid-containing liquid by bringing the (meth)acrylic acid-containing gas into contact with a collection solvent and/or condensing the (meth)acrylic acid-containing gas by cooling The (meth)acrylic acid production raw material to be subjected to the catalytic gas-phase oxidation reaction can be used without any particular limitation as long as (meth) acrylic acid is formed by reaction, and examples thereof include propane, propylene, (meth)acrolein, isobutylene and others. Acrylic acid can be obtained by, for example, oxidizing propane, propylene or acrolein in one step, or oxidizing propane or propylene via acrolein in two steps. Acrolein is not limited to that obtained by oxidizing propane or propylene, which is used as a raw material, and acrolein may be obtained by dehydrating glycerin of a raw material, for example. Methacrylic acid can be obtained by, for example, oxidizing isobutylene or methacrolein in one step, or oxidizing isobutylene via methacrolein in two steps.

As a catalyst used for the catalytic gas phase oxidation, a conventionally known catalyst can be used. For example, in the case where propylene is used as a raw material for producing acrylic acid, a complex oxide catalyst containing molybdenum and bismuth (molybdenum-bismuth catalyst) is preferably used as the catalyst. In the case where propane or acrolein is used as a raw material for producing acrylic acid, a complex oxide catalyst containing molybdenum and vanadium (molybdenum-vanadium catalyst) is preferably used as the catalyst.

As a reactor for performing the catalytic gas phase oxidation reaction, a fixed bed reactor, a fluidized bed reactor, a moving bed reactor, or the like can be used. Among these, from the viewpoint of excellent reaction efficiency, a multitubular fixed bed reactor is preferably used. In the case where (meth)acrylic acid is produced by oxidizing a (meth) acrylic acid production raw material in two steps, a reactor for performing a first oxidation reaction and a rector for performing a second oxidation reaction are combined or one reactor is divided into a region where the first oxidation reaction is performed and a region where the second oxidation reaction is performed, whereby (meth)acrylic acid is produced from a (meth)acrylic acid production raw material. In the latter case, for example in a fixed bed reactor, a catalyst for performing the first oxidation reaction may be filled in an inlet side (namely, an introducing side of the (meth)acrylic acid production raw material) of reaction tubes of the fixed bed reactor, and a catalyst for performing the second oxidation reaction may be filled in an outlet side of those.

The reaction for producing the (meth)acrylic acid-containing gas from the (meth)acrylic acid production raw material may be conducted under known reaction conditions. For example, in the case of producing acrylic acid from propylene by oxidation reaction in two steps, a propylene-containing gas is introduced into a reactor together with molecular oxygen, and for example, the first oxidation reaction may be performed under conditions of reaction temperature of 250° C. to 450° C., reaction pressure of 0 MPaG to 0.5 MPaG and space velocity of 300 $h^{-1}$ to 5000 $h^{-1}$, and then the second oxidation reaction may be performed under conditions of reaction temperature of 250° C. to 380° C., reaction pressure of 0 MPaG to 0.5 MPaG, and space velocity of 300 $h^{-1}$ to 5000 $h^{-1}$.

The (meth)acrylic acid-containing gas obtained by catalytic gas-phase oxidation reaction of the (meth)acrylic acid production raw material is brought into contact with a collection solvent and/or is condensed by cooling, thereby obtaining a (meth)acrylic acid-containing liquid. In the former case, as the (meth)acrylic acid-containing gas is introduced into a collection column and brought into contact with a collection solvent, (meth)acrylic acid is absorbed into the collection solvent, thereby obtaining the (meth)acrylic acid-containing liquid (collection step). In the latter case, as the (meth)acrylic acid-containing gas is introduced into a condensation column and cooled, (meth)acrylic acid is condensed, thereby obtaining the (meth)acrylic acid-containing liquid (condensation step).

The collection column is not particularly limited as long as the (meth)acrylic acid-containing gas can be brought into contact with the collection solvent in the collection column. For example, as the (meth)acrylic acid-containing gas is introduced into a collection column from a lower part of the collection column and the collection solvent is introduced into the collection column from an upper part of the collection column, the (meth)acrylic acid-containing gas comes into countercurrent contact with the collection solvent while rising in the collection column, and (meth)acrylic acid is absorbed by the collection solvent and recovered as the (meth)acrylic acid-containing liquid. As the collection column, for example, a tray column provided with shelves (sieve trays) in the column, a packed column filled with a packing in the column, a wet wall column in which the collection solvent is supplied to the surface of the inner wall of the column, a spray column in which the collection solvent is sprayed into the space in the column or the like can be adopted.

The collection solvent is not particularly limited as long as it can absorb and dissolve (meth)acrylic acid, and for example, diphenyl ether, diphenyl, a mixture of diphenyl ether and diphenyl, water, (meth)acrylic acid-containing water (for example, an aqueous solution containing (meth) acrylic acid obtained in the production process of (meth) acrylic acid), or the like can be used. Among them, water or (meth)acrylic acid-containing water is preferably used as the collection solvent, and more preferably, water or (meth) acrylic acid-containing water containing 50 mass % or more (more preferably 70 mass % or more, even more preferably 80 mass % or more) of water.

Temperature and the feed amount of the collection solvent may be appropriately set so that (meth)acrylic acid contained in the (meth)acrylic acid-containing gas is sufficiently absorbed by the collection solvent. Temperature of the collection solvent is preferably 0° C. or higher, more preferably 5° C. or higher, and preferably 35° C. or lower, more preferably 30° C. or lower, from the viewpoint of increasing collection efficiency of (meth)acrylic acid. Regarding the feed amount of the collection solvent, a liquid gas ratio (UG) indicated by the ratio of the feed amount (L) of the collection solvent to the collection column with respect to the introducing amount (G) of the (meth)acrylic acid-containing gas to the collection column is preferably 2 $L/m^3$ or more, more preferably 3 $L/m^3$ or more, even more preferably 5 $L/m^3$ or more, and preferably 15 $L/m^3$ or less, more preferably 12 $L/m^3$ or less, even more preferably 10 $L/m^3$ or less.

(Meth)acrylic acid absorbed by the collection solvent is withdrawn from the collection column as the (meth)acrylic acid-containing liquid. The (meth)acrylic acid-containing liquid may be withdrawn from, for example, a position below a supply position of the (meth)acrylic acid-containing gas in the collection column (for example, the bottom of the collection column).

It is preferred that the collection column is provided with a circulation path for returning a part of the (meth)acrylic acid-containing liquid discharged from the collection column to the collection column, of which returning position is located above a supply position of the (meth)acrylic acid-containing gas and a discharge position of the (meth)acrylic acid-containing liquid and below a supply position of the collection solvent in the collection column. By returning a part of the (meth)acrylic acid-containing liquid withdrawn from the collection column to the collection column through the circulation path and circulating it, (meth)acrylic acid concentration in the (meth)acrylic acid-containing liquid can be increased. The circulation path is preferably provided with a heat exchanger for cooling the (meth)acrylic acid-containing liquid flowing through the circulation path.

Meanwhile, in the case where the (meth)acrylic acid-containing liquid is obtained by condensing the (meth) acrylic acid-containing gas, a condensation column is preferably used, and as the condensation column, a heat exchanger having a heat transfer surface can be used, for example. By cooling the (meth)acrylic acid-containing gas via the heat transfer surface, (meth)acrylic acid can be condensed from the (meth)acrylic acid-containing gas, and as a result, the (meth)acrylic acid-containing liquid is obtained. A conventionally known heat exchanger may be used as the heat exchanger, and for example, a plate heat exchanger, a multitubular (shell-and-tube) heat exchanger, a double-tube heat exchanger, a coil heat exchanger, a spiral plate heat exchanger, or the like can be employed. A plurality of heat exchangers may be connected in series and the (meth)acrylic acid-containing gas may be cooled in multiple stage to perform fractional condensation, thereby recovering the (meth)acrylic acid-containing liquid.

The condensation column may be configured such that the (meth)acrylic acid-containing liquid is obtained from the (meth)acrylic acid-containing gas by bringing the (meth) acrylic acid-containing gas into contact with a condensate. In this case, it is preferable to provide a shelves (sieve trays) in the condensation column or fill the condensation column with a packing to improve contact efficiency between the (meth)acrylic acid-containing gas and the condensate. By using such a condensation column, the (meth)acrylic acid-containing gas is separated and condensed as the (meth) acrylic acid-containing gas is introduced into the condensation column from a lower part of the condensation column and moves from the lower part to the upper part of the condensation column, for example. At this time, the (meth) acrylic acid-containing liquid is withdrawn from a middle stage of the condensation column, substances having a higher boiling point than (meth)acrylic acid is withdrawn from a lower stage of the condensation column and substances having a lower boiling point than (meth)acrylic acid is withdrawn from an upper stage of the condensation column, for example. A part of the condensate withdrawn from each stage of the condensation column may be cooled by a heat exchanger or the like and then returned to the same stage of the condensation column. In general, no liquid medium other than the condensate generated in the condensation column is added to the condensate to be returned to the condensation column.

When obtaining the (meth)acrylic acid-containing liquid from the (meth)acrylic acid-containing gas, a polymerization inhibitor may be added into the collection column or the condensation column in order to suppress polymerization of (meth)acrylic acid. As the polymerization inhibitor, the polymerization inhibitors described above can be used.

In the present invention, the thus obtained (meth)acrylic acid-containing liquid can be subjected to the vaporization separation step described above. In this case, a distillation column can be adopted as the vaporization separation column since it is easier to obtain purified (meth)acrylic acid of higher purity, and in this case, the distillation column that functions as a low-boiling separation column is preferably used. The low-boiling separation column is provided with the drawn liquid circulation path at a bottom part of the column.

In the low-boiling separation column, at least a part of a low-boiling fraction is removed from the (meth)acrylic acid-containing liquid, thereby obtaining purified (meth) acrylic acid. The low-boiling fraction means a fraction having a lower boiling point than the purified (meth)acrylic acid, that is, a fraction withdrawn from a top side of the column relative to the purified (meth)acrylic acid in the low-boiling separation column. The low-boiling fraction includes a compound having a lower boiling point than (meth)acrylic acid such as water and acetic acid.

In the low-boiling separation column, it is preferable that the (meth)acrylic acid-containing liquid is introduced into the low-boiling separation column from the middle part thereof. The (meth)acrylic acid-containing liquid is preferably introduced from a position, for example, in the range of 5% or more and 75% or less of the total theoretical plate number, counted from the top side of the column in the range of from the top part to the bottom part of the low-boiling separation column, and that range is more preferably 10% or more, even more preferably 15% or more, and more preferably 70% or less, even more preferably 65% or less.

In the low-boiling separation column, the low-boiling fraction is withdrawn from the top side of the column relative to a supply position of the (meth)acrylic acid-containing liquid, preferably withdrawn from the top part of the column. The low-boiling fraction is preferably withdrawn from a position in the range of 0% or more to less than 5% of the total theoretical plate number, counted from the top side of the column in the range of from the top part to the bottom part of the low-boiling separation column. The low-boiling fraction distilled from the low-boiling separation column is preferably returned to the preceding collection column or condensation column. In returning to the collection column, though it is not particularly restricted, the low-boiling fraction is preferably returned to, for example, a position in the range of 20% or more and 90% or less, more preferably returned to a positon in the range of 30% or more and 80% or less in the entire length of the collection column, provided that the bottom of the collection column is the start point (0%) and the top of that is the end point (100%).

Meanwhile, the purified (meth)acrylic acid is withdrawn from an outlet port provided at the middle part and/or the bottom part of the low-boiling separation column. The outlet port of the purified (meth)acrylic acid is preferably provided on the bottom side of the column relative to the supply position of the (meth)acrylic acid-containing liquid, and for example, it is provided preferably in the range of 20% or more and 100% or less of the total theoretical plate number, counted from the top side of the column in the range of from the top part to the bottom part of the low-boiling separation column, and that range is more preferably 25% or more, even more preferably 35% or more. The outlet port of the purified (meth)acrylic acid is preferably provided at the middle part of the column, and in this case, since the bottom liquid containing a large amount of high-boiling components are withdrawn from the bottom part of the column, it becomes easy to increase (meth)acrylic acid concentration in the purified (meth)acrylic acid withdrawn from the middle part of the column. In this case, the outlet port of the purified (meth)acrylic acid is preferably provided in the range of 90% or less of the total theoretical plate number, counted from the top side of the column in the range of from the top part to the bottom part of the low-boiling separation column, and that range is more preferably 80% or less, even more preferably 70% or less.

In the low-boiling separation column, distillation may be performed under the conditions that a low-boiling fraction including a collection solvent, acetic acid and the like can be separated from (meth)acrylic acid, and it is preferable that temperature and pressure in the low-boiling separation column is appropriately adjusted so that such distillation can be performed. For example, pressure (absolute pressure) at the top of the column is preferably 2 kPa or higher, more preferably 3 kPa or higher, and preferably 50 kPa or lower, more preferably 40 kPa or lower, even more preferably 30 kPa or lower. Temperature at the top of the column is preferably 30° C. or higher, more preferably 40° C. or higher, and preferably 70° C. or lower, more preferably 60° C. or lower. Temperature at the bottom of the column is preferably 70° C. or higher, more preferably 80° C. or higher, and preferably 120° C. or lower, more preferably 110° C. or lower. By performing distillation under such conditions, it becomes easy to obtain the purified (meth)acrylic acid having a reduced concentration of the collection solvent or acetic acid (for example, both water concentration and acetic acid concentration are 1 mass % or less).

In distillation of the (meth)acrylic acid-containing liquid, an azeotropic solvent may be used or may not be used. However, in the case where (meth)acrylic acid concentration in the (meth)acrylic acid-containing liquid is 80 mass % or more, it is preferable that an azeotropic solvent is not used, since a low-boiling fraction is easily removed without using an azetropic solvent.

(Meth)acrylic acid concentration in the purified (meth)acrylic acid obtained from the low-boiling separation column is not particularly limited as long as it is higher than that of the (meth)acrylic acid-containing liquid; however, it is preferably, for example, 80 mass % or more, more preferably 85 mass % or more, even more preferably 90 mass % or more, and particularly preferably 92 mass % or more. The upper limit of the (meth)acrylic acid concentration in the purified (meth)acrylic acid is not particularly limited, and is usually less than 99.5 mass %.

In the production method of the present invention, the bottom liquid obtained from the low-boiling separation column may be subjected to the vaporization separation step described above. In this case, it is preferable that a distillation column that functions as a high-boiling separation column is adopted as the vaporization separation column. The bottom liquid of the low-boiling separation column contains (meth)acrylic acid at a considerable concentration and further contains a large amount of components having higher boiling point than (meth)acrylic acid, such as Michael adducts and maleic acid, and therefore, when the bottom liquid of the low-boiling separation column is introduced into the high-boiling separation column and distilled, a (meth)acrylic acid-containing distillate having reduced high-boiling components can be obtained. In this case, the bottom liquid of the low-boiling separation column comes to be the (meth)acrylic acid-containing liquid, and the (meth)acrylic acid-containing distillate comes to be the purified (meth)acrylic acid. The (meth)acrylic acid-containing distillate is preferably returned to the low-boiling separation column, and thereby, yield of (meth)acrylic acid as a whole process can be increased.

In the bottom part of the high-boiling separation column, a bottom liquid in which high-boiling components such as Michael adducts are concentrated is generated. It is preferable that this bottom liquid is withdrawn from the bottom part of the high-boiling separation column and introduced into a (meth)acrylic acid dimer decomposition apparatus. Since the Michael adduct contained in the bottom liquid can be reverted to (meth)acrylic acid by thermal decomposition, it is preferable that the bottom liquid is introduced into a (meth)acrylic acid dimer decomposition apparatus and thermally decomposed, and thus obtained decomposed liquid is returned to the high-boiling separation column again.

The (meth)acrylic acid dimer decomposition apparatus is composed of a pyrolysis tank, and the bottom liquid of the high-boiling separation column is heated in the (meth)acrylic acid dimer decomposition apparatus at a temperature of 120° C. or higher and 220° C. or lower (preferably 140° C. or higher and 200° C. or lower), whereby the Michael adduct contained in the bottom liquid can be decomposed.

For accelerating the decomposition of the Michael adduct, it is preferable that a decomposition catalyst such as an alkali metal salt, an alkaline earth metal salt or an N-oxyl compound described in Japanese Unexamined Patent Application Publication No. 2003-89672 is added into the pyrolysis tank. In particular, when an N-oxyl compound is used as a polymerization inhibitor in the low-boiling separation column or the preceding collection or condensation column, it can also act as a decomposition catalyst for the Michael adducts, which is preferable.

In the high-boiling separation column, at least a part of the bottom liquid in which high-boiling components are concentrated can be withdrawn, heated by a reboiler provided in the drawn liquid circulation path, and returned to the high-boiling separation column. In the case where the Michael adduct contained in the bottom liquid is decomposed in the (meth)acrylic acid dimer decomposition apparatus, the decomposed liquid may be returned to the high-boiling separation column via the reboiler, and the drawn liquid of the bottom liquid heated by the reboiler may be introduced into the (meth)acrylic acid dimer decomposition apparatus (pyrolysis tank).

The purified easily polymerizable compound obtained in the vaporization separation step may be subjected to another purification step, may be handled as a product without further purification, or may be used as a raw material for producing other compounds. In the former case, crystallization is preferably employed in the purification step since it is easy to obtain the easily polymerizable compound with higher purity while suppressing polymerization of the easily polymerizable compound.

Crystallization may be performed batchwise or continuously. As a crystallizer used in the crystallization operation, a crystallizer having a heat transfer surface, wherein an easily polymerizable compound is crystallized and/or melted by heat-exchange via the heat transfer surface, for example. When a cooling medium is supplied to one side of the heat transfer surface and the purified easily polymerizable compound obtained in the vaporization separation step is supplied to the other side of the heat transfer surface, the purified easily polymerizable compound-containing solution is cooled by heat-exchange via the heat transfer surface and the easily polymerizable compound is crystallized. In a batch crystallization operation, a heating medium is supplied to the one side of the heat transfer surface and the crystallized easily polymerizable compound is heated by heat-exchange via the heat transfer surface and a melt containing the easily polymerizable compound is obtained. Melting of the easily polymerizable compound may be performed by heating the same heat transfer surface used for crystallization, or the crystallized easily polymerizable compound is collected and the collected easily polymerizable compound crystal may be heated via another heat transfer surface which is different from one used for crystallization.

In the batch crystallization operation, the easily polymerizable compound is crystallized by cooling the purified easily polymerizable compound obtained in the vaporization separation step, and the crystallized easily polymerizable compound is melted to obtain a melt containing the easily polymerizable compound. At this time, in order to increase purity of the easily polymerizable compound melt to be obtained, it is preferable that the easily polymerizable compound crystals are first partially melted (sweated), whereby impurities present between the crystals or on the surface of the crystals are washed away, and then the easily polymerizable compound melt is recovered by melting the remaining easily polymerizable compound crystals. A non-crystalline residue that is generated in cooling the easily polymerizable compound and a sweated solution obtained by partially melting the easily polymerizable compound crystals is preferably discharged from the crystallizer as a crystallizing residue. As a crystallizer used in the batch crystallization operation, for example, a layer crystallization apparatus (dynamic crystallizer) manufactured by Sulzer Chemtech Ltd., a static crystallization apparatus manufactured by BEFS PROKEM, or the like can be used.

In the continuous crystallization operation, for example, the purified easily polymerizable compound obtained in the vaporization separation step is continuously supplied to a crystallizer and cooled to crystallize the easily polymerizable compound, a slurry composed of easily polymerizable compound crystals and a mother liquor is continuously discharged from the crystallizer, and the slurry is supplied to a washing column to continuously separate the easily polymerizable compound crystals from the mother liquor while washing. As a crystallizer used in the continuous crystallization operation, a crystallization apparatus in which a crystallization part, a solid-liquid separation part and a crystal purification part are united (e.g., a BMC (Backmixing Column Crystallizer) apparatus); a crystallization apparatus in combination with a crystallization part (e.g., CDC crystallization apparatus (Cooling Disc Crystallizer) manufactured by GOUDA) a DC crystallization apparatus (Drum Crystallizer) manufactured by GEA, a solid-liquid separation part (e.g., a belt filter or a centrifugal separator) and a crystal purification part (e.g., KCP refiner (Kureha Crystal Purifier) manufactured by Kureha Engineering Co., Ltd. and a WC (Wash Column) refiner manufactured by GEA Inc.); or the like can be used.

The crystallizing residue generated in the crystallization step is preferably returned to the preceding vaporization separation step, particularly the low-boiling separation column. Meanwhile, the high-purity easily polymerizable compound obtained in the crystallization step may be further purified by any purification means, however, it is preferably handled as a product or used as a raw material for producing other compounds without further purification.

This application claims priority to Japanese Patent Applications No. 2020-098798 and No. 2020-098800, filed on Jun. 5, 2020. All of the contents of the Japanese Patent Applications No. 2020-098798 and No. 2020-098800, filed on Jun. 5, 2020, are incorporated by reference herein.

EXAMPLES

The present invention is hereinafter described more specifically by reference to Examples; however, the present invention is not limited to these Examples.

Example 1

An acrylic acid-containing liquid (crude acrylic acid) containing hydroquinone and hydroquinone monomethyl ether was supplied to a distillation column and purified by distillation. The distillation column was provided with a circulation path for a bottom liquid of the column, and the circulation path was provided with a reboiler having a vertical shell-and-tube heat exchanger. A part of the bottom liquid of the distillation column was withdrawn, heated with the reboiler, and returned to the distillation column, whereby the bottom liquid was heated. The distillation column was operated under the conditions that the pressure at the bottom part of the column was 23 kPa, the pressure at an inlet of the heating part of the reboiler was 62 kPa, and the temperature at the bottom part of the column was 95° C. to 105° C., and the bottom liquid of the column contained 90% or more of acrylic acid, 1300 ppm of hydroquinone and 250 ppm of hydroquinone monomethyl ether. An oxygen nozzle was provided in the circulation path on the upstream side of the reboiler, and oxygen gas was supplied to a circulating liquid flowing in the circulation path at 9 $Nm^3/h$ (gas volume/circulating liquid volume=13%). A supply port of the oxygen nozzle was located 1850 mm below the inlet of the heat exchanger (heating part), the pressure of the circulating liquid at the supply port of the circulation path was 80 kPa, and the average retention time of the circulating liquid was 5.1 seconds. After operating for about 6 months, the operation was stopped and the inside of the distillation column and the heat exchanger were inspected, resulting in that no polymer was found.

Comparative Example 1

In Example 1, the supply port of the oxygen nozzle was installed so as to be located 250 mm below the inlet of the heat exchanger, and the operation was conducted under the condition that the pressure of the circulating liquid at the supply port was 64 kPa. After operating for about 6 months, the operation was stopped and the inside of the distillation column and the heat exchanger were inspected, resulting in that more than 70% of the total number of heat exchanger tubes in the heat exchanger were clogged with polymer.

Example 2

An acrylic acid-containing liquid (crude acrylic acid) containing hydroquinone and hydroquinone monomethyl ether was supplied to a distillation column and purified by distillation. The distillation column was provided with a circulation path for a bottom liquid of the column, and the circulation path was provided with a reboiler having a vertical shell-and-tube heat exchanger. A part of the bottom liquid of the distillation column was withdrawn, heated with the reboiler, and returned to the distillation column, whereby the bottom liquid was heated. The distillation column was operated under the conditions that the pressure at the bottom part of the column was 15 kPa, the pressure at an inlet of the heating part of the reboiler was 54 kPa, and the temperature at the bottom part of the column was 80° C. to 90° C., and the bottom liquid of the column contained 90% or more of acrylic acid, 1600 ppm of hydroquinone and 250 ppm of hydroquinone monomethyl ether. An oxygen nozzle was provided in the circulation path on the upstream side of the reboiler, and oxygen gas was supplied to a circulating liquid flowing in the circulation path at 3 $Nm^3/h$ (gas volume/circulating liquid volume=5%). A supply port of the oxygen nozzle was located 1750 mm below the inlet of the heat exchanger (heating part), the pressure of the circulating liquid at the supply port of the circulation path was 71 kPa, and the average retention time of the circulating liquid was 5.2 seconds. After operating for about 6 months, the operation was stopped and the inside of the distillation column and the heat exchanger were inspected, resulting in that no polymer was found.

Comparative Example 2

In Example 2, the supply port of the oxygen nozzle was installed so as to be located 250 mm below the inlet of the heat exchanger, and the operation was conducted under the condition that the pressure of the circulating liquid at the supply port was 57 kPa. After operating for about 6 months, the operation was stopped and the inside of the distillation column and the heat exchanger were inspected, resulting in that more than 50% of the total number of heat exchanger tubes in the heat exchanger were clogged with polymer.

Example 3

An acrylic acid-containing liquid (crude acrylic acid) containing hydroquinone was supplied to a distillation column and purified by distillation. The distillation column was provided with a circulation path for a bottom liquid of the column, and the circulation path was provided with a reboiler having a vertical shell-and-tube heat exchanger. A part of the bottom liquid of the distillation column was withdrawn, heated with the reboiler, and returned to the distillation column, whereby the bottom liquid was heated. The distillation column was operated under the conditions that the pressure at the bottom part of the column was 14 kPa, the pressure at an inlet of the heating part of the reboiler was 53 kPa, and the temperature at the bottom part of the column was 80° C. to 90° C., and the bottom liquid of the column contained 90% or more of acrylic acid, 1300 ppm of hydroquinone. An oxygen nozzle was provided in the circulation path on the upstream side of the reboiler, and oxygen gas was supplied to a circulating liquid flowing in the circulation path at 3 $Nm^3/h$ (gas volume/circulating liquid volume=10%). A supply port of the oxygen nozzle was located 1800 mm below the inlet of the heat exchanger (heating part), the pressure of the circulating liquid at the supply port of the circulation path was 71 kPa, and the average retention time of the circulating liquid was 5.3 seconds. After operating for about 6 months, the operation was stopped and the inside of the distillation column and the heat exchanger were inspected, resulting in that no polymer was found.

Comparative Example 3

In Example 3, the supply port of the oxygen nozzle was installed so as to be located 400 mm below the inlet of the heat exchanger, and the operation was conducted under the condition that the pressure of the circulating liquid at the supply port was 58 kPa. After operating for about 6 months, the operation was stopped and the inside of the distillation column and the heat exchanger were inspected, resulting in that more than 40% of the total number of heat exchanger tubes in the heat exchanger were clogged with polymer.

Example 4

A methyl acrylate-containing liquid (crude methyl acrylate) containing hydroquinone and hydroquinone monomethyl ether was supplied to a distillation column and purified by distillation. The distillation column was provided with a circulation path for a bottom liquid of the column, and the circulation path was provided with a reboiler having a vertical shell-and-tube heat exchanger. A part of the bottom liquid of the distillation column was withdrawn, heated with the reboiler, and returned to the distillation column, whereby the bottom liquid was heated. The distillation column was operated under the conditions that the pressure at the bottom part of the column was 120 kPa, the pressure at an inlet of the heating part of the reboiler was 140 kPa, and the temperature at the bottom part of the column was 75° C. to 85° C., and the bottom liquid of the column contained 90% or more of methyl acrylate, 500 ppm of hydroquinone and 30 ppm of hydroquinone monomethyl ether. An oxygen nozzle was provided in the circulation path on the upstream side of the reboiler, and air was supplied to a circulating liquid flowing in the circulation path at 6 $Nm^3/h$ (gas volume/circulating liquid volume=4%). A supply port of the oxygen nozzle was located 2300 mm below the inlet of the heat exchanger (heating part), the pressure of the circulating liquid at the supply port of the circulation path was 160 kPa, and the average retention time of the circulating liquid was 5 seconds. After operating for about one year, the operation was stopped and the inside of the distillation column and the heat exchanger were inspected, resulting in that no polymer was found.

Comparative Example 4

In Example 4, the supply port of the oxygen nozzle was installed so as to be located 200 mm below the inlet of the heat exchanger, and the operation was conducted under the condition that the pressure of the circulating liquid at the supply port was 140 kPa. After operating for about one year, the operation was stopped and the inside of the distillation column and the heat exchanger were inspected, resulting in that more than 5% of the total number of heat exchanger tubes in the heat exchanger were clogged with polymer.

Example 5

A methyl acrylate-containing liquid (crude methyl acrylate) containing hydroquinone and hydroquinone monomethyl ether was supplied to a distillation column and purified by distillation. The distillation column was provided with a circulation path for a bottom liquid of the column, and the circulation path was provided with a reboiler having a vertical shell-and-tube heat exchanger. A part of the bottom liquid of the distillation column was withdrawn, heated with the reboiler, and returned to the distillation column, whereby the bottom liquid was heated. The distillation column was operated under the conditions that the pressure at the bottom part of the column was 140 kPa, the pressure at an inlet of the heating part of the reboiler was 170 kPa, and the temperature at the bottom part of the column was 75° C. to 85° C., and the bottom liquid of the column contained 90% or more of methyl acrylate, 500 ppm of hydroquinone and 30 ppm of hydroquinone monomethyl ether. An oxygen nozzle was provided in the circulation path on the upstream side of the reboiler, and air was supplied to a circulating liquid flowing in the circulation path at 6 $Nm^3/h$ (gas volume/circulating liquid volume=4%). A supply port of the oxygen nozzle was located 1000 mm below the inlet of the heat exchanger (heating part), the pressure of the circulating liquid at the supply port of the circulation path was 170 kPa, and the average retention time of the circulating liquid was 3 seconds. After operating for about one year, the operation was stopped and the inside of the distillation column and the heat exchanger were inspected, resulting in that no polymer was found.

REFERENCE SIGNS LIST

1: vaporization separation column
2: circulation path
3: bottom liquid
4: reboiler
5: heating part
6: widened portion
7: supply port (of oxygen-containing gas)
8: bent portion

The invention claimed is:

1. A method for producing an easily polymerizable compound,
- comprising a step of introducing an easily polymerizable compound-containing liquid into a vaporization separation column selected from a distillation column and a stripping column to purify, wherein:
- the vaporization separation column is provided with a circulation path for returning a drawn liquid, obtained by withdrawing at least a part of a bottom liquid of the column, to the vaporization separation column;
- the circulation path is provided with a supply port for supplying an oxygen-containing gas and a reboiler having a heating part, in order, from an upstream side;
- the supply port is located below an inlet of the heating part, with a height difference of 1.5 m or more; and
- an oxygen-containing gas is supplied to the drawn liquid from the supply port.

2. The method for producing an easily polymerizable compound according to claim 1, wherein the easily polymerizable compound-containing liquid is introduced into the vaporization separation column and purified under reduced pressure.

3. The method for producing an easily polymerizable compound according to claim 1, wherein the easily polymerizable compound-containing liquid is introduced into the vaporization separation column and purified under normal pressure or increased pressure.

4. The method for producing an easily polymerizable compound according to claim 1, wherein a pressure of the drawn liquid at the supply port is 30 kPa or more higher than a gas pressure on an upper surface of the bottom liquid.

5. The method for producing an easily polymerizable compound according to claim 1, wherein an average retention time of the drawn liquid from the supply port of the circulation path to the inlet of the heating part is 2 seconds or longer.

6. The method for producing an easily polymerizable compound according to claim 1, wherein the circulation path has a bent portion between the supply port and the heating part.

7. The method for producing an easily polymerizable compound according to claim 1, wherein the supply port is provided in a horizontal portion where the circulation path extends substantially horizontally.

8. The method for producing an easily polymerizable compound according to claim 7, wherein an average retention time of the drawn liquid in the horizontal portion is 0.5 seconds or longer.

9. The method for producing an easily polymerizable compound according to claim 1, wherein a widened portion is provided at a connection between the circulation path on an upstream side of the heating part and the heating part.

10. The method for producing an easily polymerizable compound according to claim 1, wherein the reboiler having the heating part is composed of a plate heat exchanger, a shell-and-tube heat exchanger, a double-tube heat exchanger, a coil heat exchanger, or a spiral heat exchanger.

11. The method for producing an easily polymerizable compound according to claim 1, wherein the oxygen-containing gas is supplied as microbubbles.

12. The method for producing an easily polymerizable compound according to claim 1, wherein the easily polymerizable compound is (meth)acrylic acid or (meth)acrylic acid ester.

* * * * *